United States Patent
Bonadio

[11] Patent Number: 5,899,208
[45] Date of Patent: May 4, 1999

[54] HAND ACCESS PORT

[75] Inventor: Frank Bonadio, Bray, Ireland

[73] Assignee: Gaya Limited, Dublin, Ireland

[21] Appl. No.: 08/808,160

[22] Filed: Feb. 28, 1997

Related U.S. Application Data

[63] Continuation of application No. 08/433,498, May 8, 1995, Pat. No. 5,803,921.

[30] Foreign Application Priority Data

Mar. 1, 1996 [IE] Ireland .................................. S960196

[51] Int. Cl.$^6$ .................................................. A61B 19/00
[52] U.S. Cl. ........................... 128/897; 128/850; 604/174
[58] Field of Search ........................ 600/21–22; 128/897, 128/846, 850–56; 604/167, 174, 178, 237, 256; 606/213, 215

[56] References Cited

U.S. PATENT DOCUMENTS

| | | |
|---|---|---|
| 2,219,564 | 10/1940 | Reyniers . |
| 2,835,253 | 5/1958 | Borgeson . |
| 4,096,853 | 6/1978 | Weigand . |
| 4,550,713 | 11/1985 | Hyman . |
| 4,998,538 | 3/1991 | Charowsky et al. . |
| 5,176,649 | 1/1993 | Wakabayashi . |
| 5,178,162 | 1/1993 | Bose . |
| 5,234,455 | 8/1993 | Mulhollan . |
| 5,242,412 | 9/1993 | Blake, III . |
| 5,275,615 | 1/1994 | Rose . |
| 5,304,203 | 4/1994 | El-Mallawany et al. . |
| 5,366,478 | 11/1994 | Brinkerhoff et al. . |
| 5,391,156 | 2/1995 | Hildwein et al. . |
| 5,480,410 | 1/1996 | Cuschieri et al. . |
| 5,511,564 | 4/1996 | Wilk . |
| 5,514,133 | 5/1996 | Golub et al. . |
| 5,640,977 | 6/1997 | Leahy et al. ............................. 128/897 |

FOREIGN PATENT DOCUMENTS

| | | |
|---|---|---|
| 0142262 | 5/1985 | European Pat. Off. . |
| 3737121 | 5/1989 | Germany . |
| 2275420 | 8/1994 | United Kingdom . |
| WO 8606272 | 11/1986 | WIPO . |
| WO 9221292 | 12/1992 | WIPO . |
| WO 9305740 | 4/1993 | WIPO . |
| WO 9507056 | 3/1995 | WIPO . |

*Primary Examiner*—John P. Lacyk
*Attorney, Agent, or Firm*—Sixbey, Friedman, Leedom & Ferguson; Daniel W. Sixbey

[57] ABSTRACT

The hand access port 10 comprises a sleeve 12, having a proximal end 13 and a distal end 14. A flange 15 is located towards the distal end and is used to secure the device to a patient's body. Above the flange 15 is an inflatable chamber 16 having an entry opening 17 through which a surgeon's hand can enter. An insufflation valve 20 in provided on the outer sleeve of the chamber 16 so that the chamber can be inflated prior to the insertion of the surgeon's hand into the device. Beneath the flange 15 is the tensioning device 30 which comprises a pair of identical arcuate bands 32 which are engaged together through two orifices at each side of the edges of the inner sleeve 11 which protrudes into the patient's body. Each band is formed with a bend 40 formed in the middle with two male studs 42 at one end and two orifices 43 at the other end. The tensioning device 30 is formed by reversing two bands 42 so that the male studs 42 engage in the orifice 43 of the other band.

7 Claims, 5 Drawing Sheets

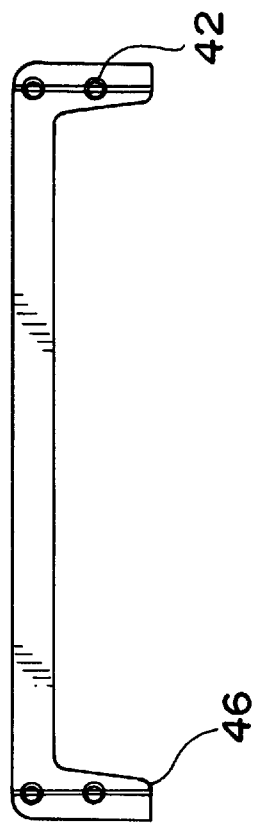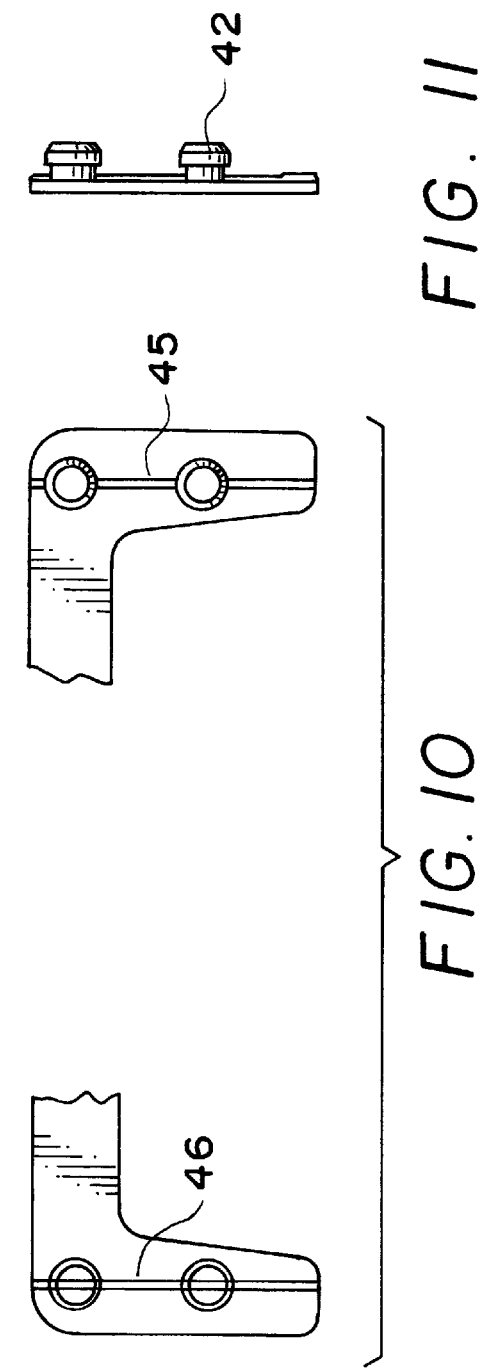
FIG. 8  FIG. 9  FIG. 10  FIG. 11

HAND ACCESS PORT

This application is a continuation of Ser. No. 08/433,498 filed May 8, 1995 now U.S. Pat. No. 5,803,921.

The present invention relates to an improved hand access port which enables hand access during laproscopic surgery while retaining pneumoperitioneum. This invention is an improvement over the invention described in detail in WO-A-9522289, published on Aug. 24 1995, the contents of which are incorporated herein by reference.

SUMMARY OF THE INVENTION

The present invention provides an access port device for use in surgery comprising a sleeve having an entry opening located at a proximal end of the sleeve, an exit opening located at a distal end thereof for insertion into an incision made in a patient's body, the exit opening allowing access to the patient's body cavity and exit opening sealing means provided by the sleeve being collapsible by gas pressure within the abdominal cavity of the patient at or adjacent the distal edges of the sleeve, whereby when the patient's body cavity is inflated by gas, the exit sealing means prevents substantial leakage of gas from the patient's body cavity while providing access for a surgeon's hand or surgical instrument and entry sealing means comprising an inflatable chamber provided on the proximal end of the sleeve for sealing the device in the region of the entry opening, so that when the patient's body cavity is inflated by gas, the entry sealing means assists in preventing substantial leakage of gas from the patient's body cavity while providing access for a surgeon's hand and sealing about the arm remaining outside the access port device, characterised in that an insufflation valve is provided on an outer surface of the inflatable chamber to allow the chamber to be inflated prior to the insertion of the surgeon's hand into the device.

Conveniently, the sleeve comprises sheets of flexible, gas impermeable, sterilisable, biocompatible material which are collapsible by gas pressure within the abdominal cavity of the patient at or adjacent, the distal edges of the sleeve and in which a separate tensioning device is provided in the distal region of the sleeve spaced from the distal edge to place the sheets under a generally transverse tension thereby creating a taut region across the sleeve operable as a further seal as part of the exit sealing means, the tensioning device comprising a pair of opposed arcuate bands operable to prevent retraction of the sleeve and in which wings are provided at the side edges of the sleeve to provide anchoring points for the opposed arcuate bands, each band having a band intermediate a pair of male studs on one wing and two orifices on the other wing, the studs of one band being engageable in the orifice of the other band to form the tensioning device.

Advantageously, the region of the band having the studs has a ridge engageable with a corresponding groove provided in the region of the band having orifices, thereby providing further means for locating and locking the two bands together.

Preferably, the sleeve is provided with a flange having adhesive thereon for affixing the access port externally to the patient.

Conveniently, the flange is located between the proximal and distal ends of the sleeve so that in use, when the flange is adhered to the patient's body, the distal end of the sleeve is inserted through the incision and is inside the patient's body cavity and the access port projects a short distance above the patient's body.

Advantageously, the sleeve has an area between the distal end and the proximal end on which, when the distal end of the sleeve is inserted through the incision, the patient's muscle tissue around the incision acts as sealing means for assisting in sealing the intermediate portion of the sleeve between the distal end and the proximal end.

Preferably, the inflatable chamber is arranged in surrounding relation to the sleeve and is capable of exerting a pressure on the sleeve causing at least a portion of it to collapse thereby sealing the entry opening.

Conveniently, the inflatable chamber is in fluid communication with the sleeve, so that in use the chamber is in fluid communication with the patient's body cavity and thus the pressure inside the inflatable chamber is equivalent to the pressure inside the patient's body cavity.

Advantageously, the sleeve and inflatable chamber are co-axial and include sheets of gas permeable flexible material bonded at their common proximal end and side edges, with the sleeve being within the inflatable chamber in the proximal region.

Preferably, the chamber is defined between an outer sleeve located about the inner sleeve in the proximal region of the device and located within the inner sleeve and extending from the proximal end toward the distal end is a flap valve formed between two further sheets of flexible material.

Conveniently, the distal edges of the flap valve are of a feathered construction and the sheets and edges of the flap valve are collapsible towards each other to form a seal when the chamber is pressurized.

Advantageously, the flap valve is connected to the inner and outer sleeves at two locations along each side thereof whereby the region of the flap valve between the two locations can conform about a portion of the surgeons hand or arm.

Preferably, the inner and outer sleeves are connected together by joins at specific locations so as to divide the inflatable chamber into upper and lower sub-chambers in fluid communication so that when pressurised, the sub-chambers define at least one contiguous seal of surfaces forming the entry sealing means or a part thereof.

Conveniently, the joins comprise a plurality of opposed welds.

The invention will now be more particularly described with reference to the accompanying drawings, which show, by way of example only, one embodiment of a hand access port according to tho invention.

BRIEF DESCRIPTION OF THE DRAWINGS

FIGS. 7, 8, 9, 10 and 11 respectively are a plan view of one of the bands before application to the device, an end view, a front view, an exploded detailed view and side view showing the engaging means of the bands.

DESCRIPTION OF THE PREFERRED EMBODIMENT

Figure 1:
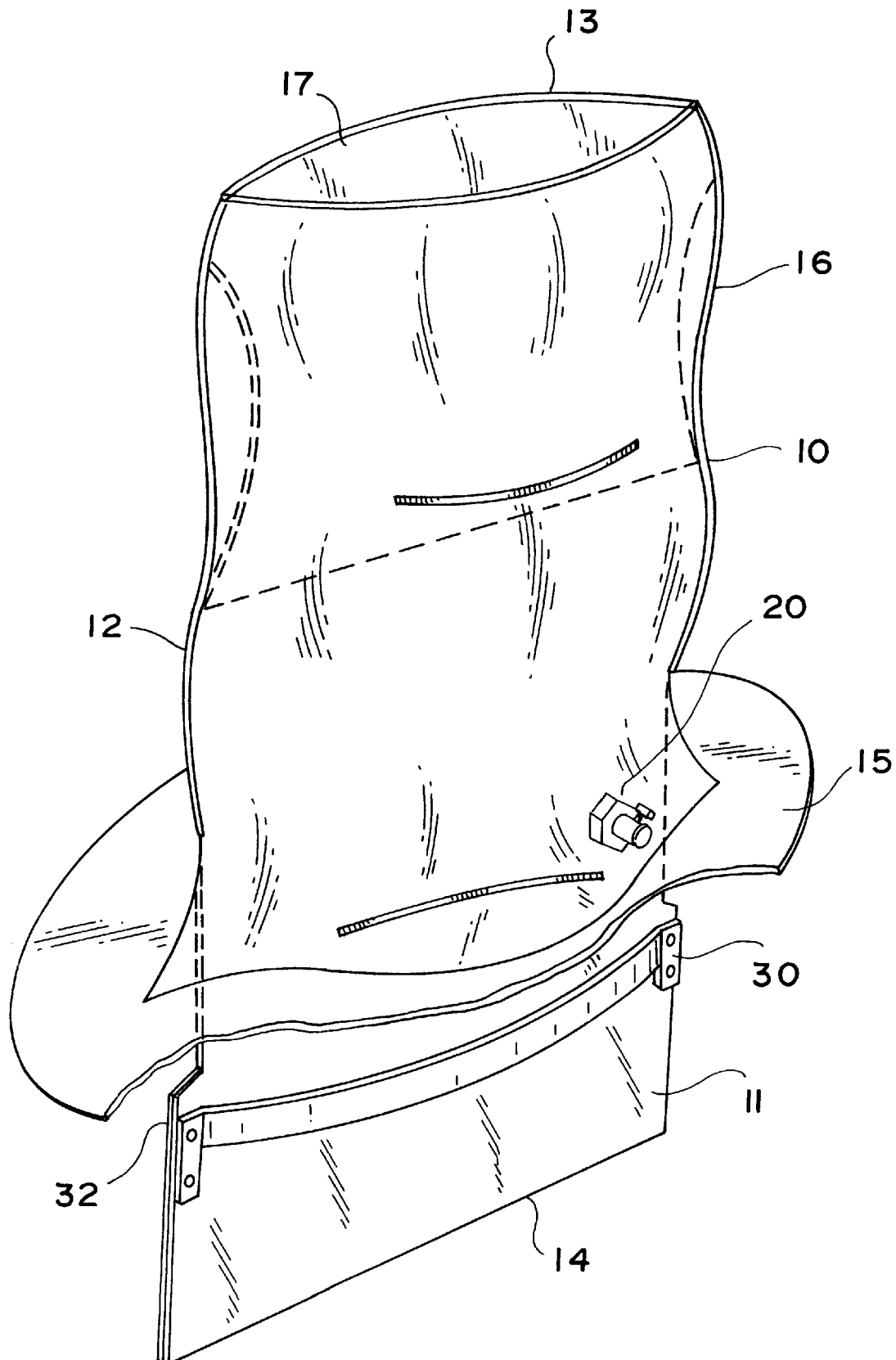
FIG. 1 is a perspective view of the hand access port.

Referring to the drawings, the hand access port according to the invention is indicated generally by reference numeral 10 and comprises a sleeve 12, having a proximal end 13 and a distal end 14. A flange 15 is located towards the distal end and is used to secure the device to a patient's body. Above the flange 15 is an inflatable chamber 16 having an entry opening 17 through which a surgeon's hand can enter. The operation of the device is described in detail in above mentioned International Publication No. WO-A-9522289.

Figure 5:
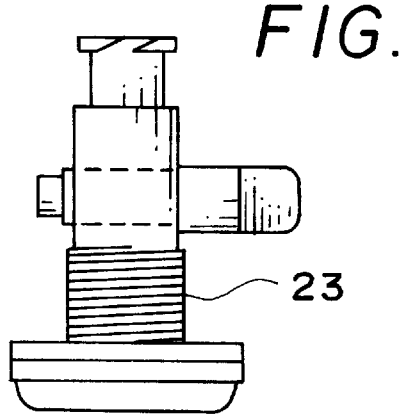
FIGS. 4, 5 and 6 are a perspective view, side view and end view respectively of the insufflation valve used in the device.
Figure 4:
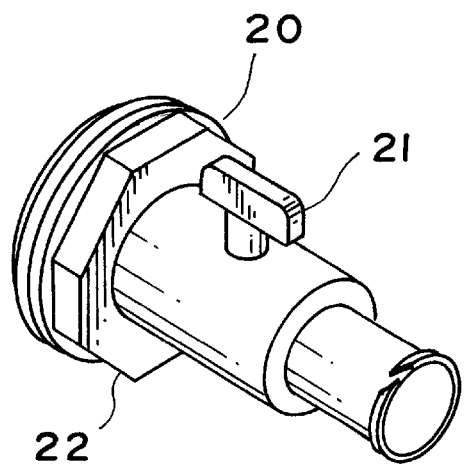
Figure 6:
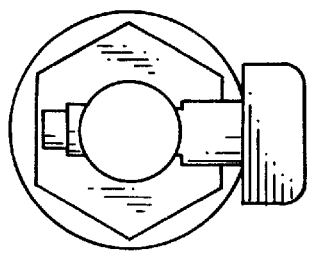

In this invention, an insufflation valve 20 is provided on the outer sleeve of the chamber 16 so that the chamber can be inflated prior to the insertion of the surgeon's hand into the device. The gas pressure in the chamber 16 is maintained from gas flowing from the body cavity of the patient during pneumoperitoneum. After the initial inflation of the chamber 16 through the insufflation valve 20, the valve is closed and the pressure of the chamber is maintained as described. Details of the valve 20 are shown in FIGS. 4, 5 and 6. A knob 21 is provided for opening and closing the valve as desired and is held In position by a ring nut 22, screwed onto a shaft 23 engaged in a hole in the outer sleeve of the chamber 16.

Figure 2:
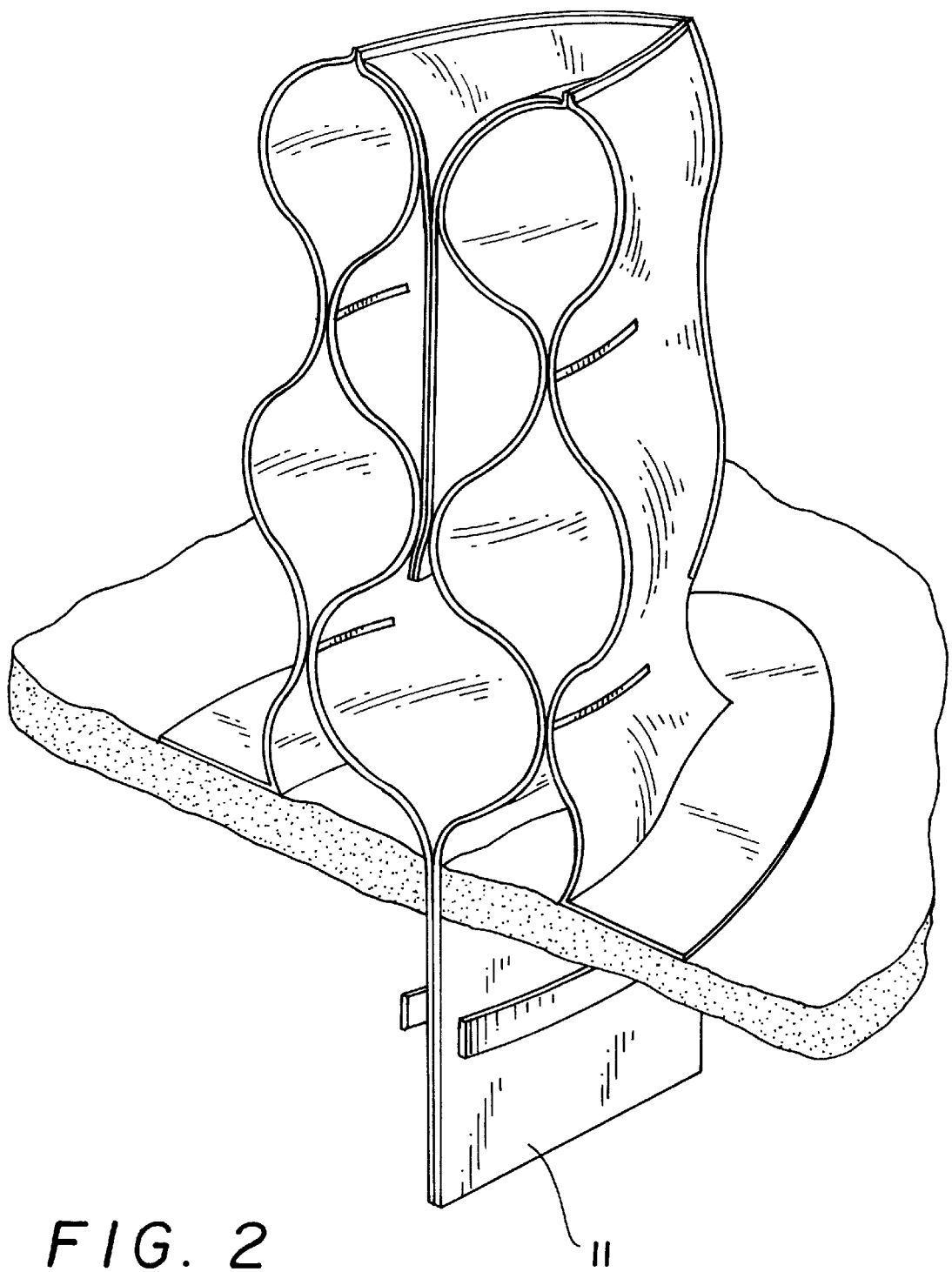
FIG. 2 is a cross-sectional view of the hand access port in position on a patient's body.
Figure 3:
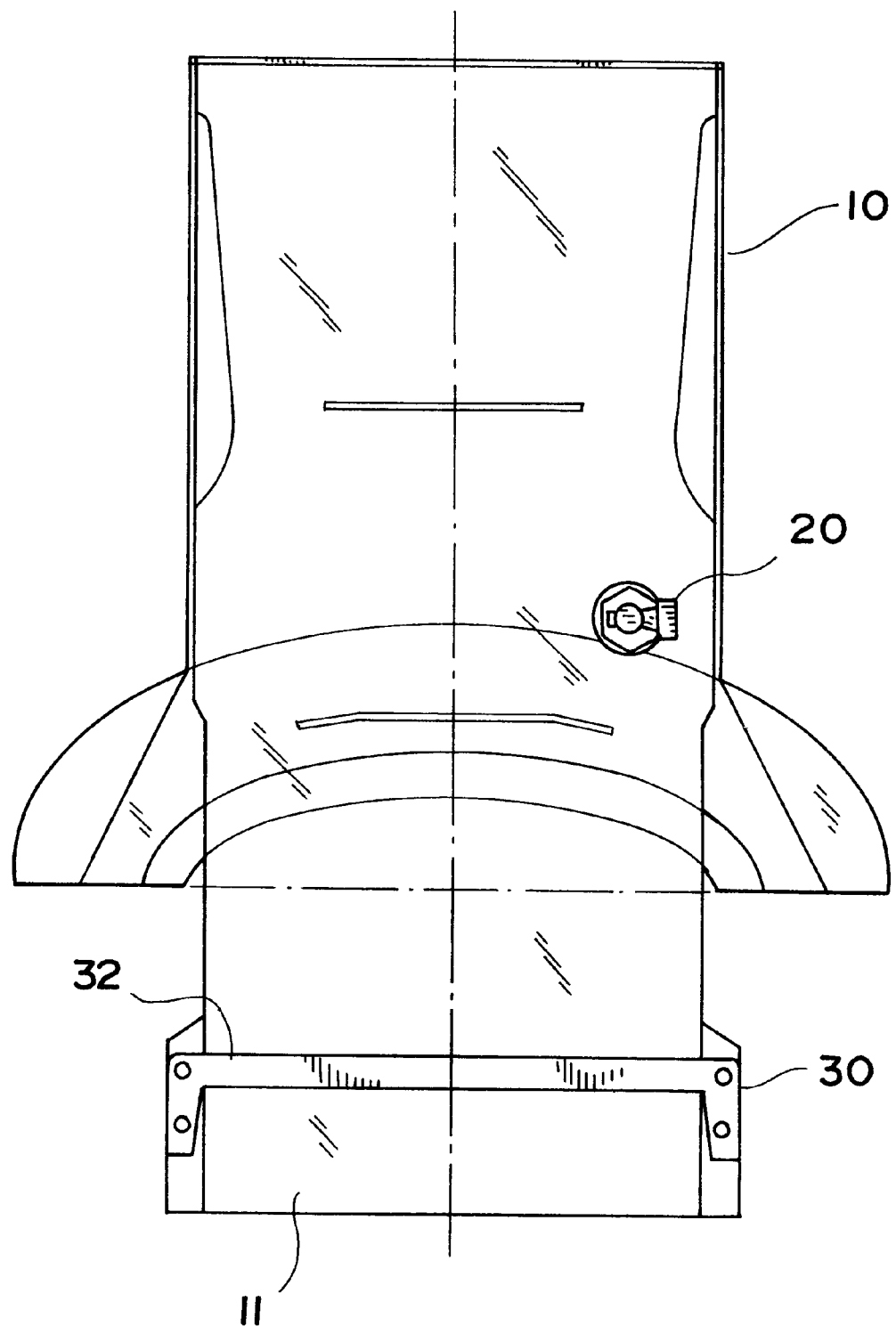
FIG. 3 is a front elevation of the hand access port showing an end view of an insufflation valve and a pair of arcuate bands which act to provide a taut valve.

Beneath the flange 15 is the tensioning device 30 which comprises a pair of identical arcuate bands 32 which are engaged together through two orifices at each side of the edges of the inner sleeve 11 which protrudes into the patient's body in FIG. 2. The two bands 32 apply a lateral pull to the sleeve 11 bringing the opposing faces of the sleeve into mutual contact and form an initial seal without the action of insuflation pressure. The geometry of the bands 32 is such that when presented at right angles to the incision made in the patient's body, it is possible for them to pass through the incision. Once in position within the abdomen, the bands 32 align themselves normally parallel to the abdominal wall. In this way, the device is anchored in position and the bands provide the final seal by means of a taut valve through which a surgeon's hand must pass when entering the patient's body. The other seals are formed after insuflation of the device.

Figure 7:
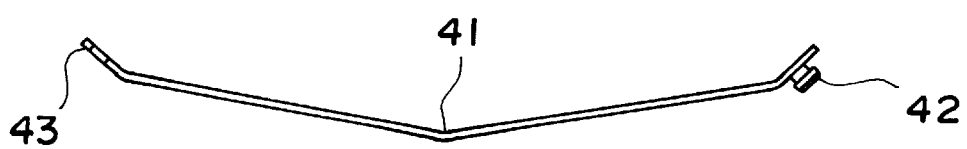

As shown in FIG. 7, each band is formed with a bend 40 formed in the middle with two male studs 42 at one end and two orifices 43 at the other end. The tensioning device 30 is formed by reversing two bands 42 so that the male studs 42 engage in the orifice 43 of the other band. When they are fully engaged, the band effectively flips over so as to become a generally concave construction formed from two convex bands. The resilience in the material and the shape of the bands causes the tension which provides the taut valve effect in the device. The material used in the particular embodiment is PETG.

As shown in FIG. 10, the region of the band carrying the studs 32 has an elongate ridge 45 which seats in groove 46 of the part carrying the orifices 43. This provides a further location means and assistance in locking two bands together. The studs 42 engage in the orifices 46 through holes provided in the sleeve 11.

It will of course be understood that the invention is not limited to the specific details described herein, which are given by way of example only, and that various modifications and alterations are possible within the scope of the invention as defined in the appended claims.

I claim:

1. An access port device for use in surgery comprising a sleeve having an entry opening located at a proximal end of the sleeve, said sleeve having distal edges opposite said entry opening to form an exit opening located at a distal end thereof for insertion into an incision made in a patient's body, the exit opening allowing access to the patient's body cavity and exit opening sealing means provided by the sleeve being collapsible by gas pressure within the abdominal cavity of the patient at or adjacent the distal edges of the sleeve, whereby when the patient's body cavity is inflated by gas, the exit sealing means prevents substantial leakage of gas from the patient's body cavity while providing access for a surgeon's hand or surgical instrument sad sleeve being formed by sheets of flexible, gas impermeable, sterilisable, biocompatible material which are collapsible by gas pressure within the abdominal cavity of the patient at or adjacent, the distal edges of the sleeve, said sheets having side edges which are joined together and formed to provide laterally projecting wings adjacent to but in spaced relation to said exit opening, a separate tensioning device provided in the distal region of the sleeve spaced from the distal edge thereof to place the sheets under a generally transverse tension thereby creating a taut region across the sleeve operable as a further seal as part of the exit sealing means, the tensioning device comprising a pair of opposed arcuate bands operable to prevent retraction of the sleeve, said wings at the side edges of the sleeve providing anchoring points for the opposed arcuate bands, each band having a bend intermediate a pair of male studs on one wing and two orifices on the other wing the studs of one band being engageable in the orifice of the other band to form the tensioning device, an entry sealing means comprising an inflatable chamber provided on the proximal end of the sleeve for sealing the device in the region of the entry opening, so that when the patient's body cavity is inflated by gas, the entry sealing means assists in preventing substantial leakage of gas from the patient's body cavity while providing access for a surgeon's hand and sealing about the arm remaining outside the access port device, and an insufflation valve provided on an outer surface of the inflatable chamber to allow the chamber to be inflated prior to the insertion of the surgeon's hand into the device.

2. An access port as claimed in claim 1, in which the region of the band having the studs has a ridge engageable with a corresponding groove provided in the region of the band having orifices, thereby providing further means for locating and locking the two bands together.

3. An access port as claimed in claim 1, wherein the sleeve is provided with a flange having adhesive thereon for affixing the access port externally to the patient.

4. An access port as claimed in claim 3, wherein the flange is located between the proximal and distal ends of the sleeve so that in use, the flange is adapted to be adhered to the patient's body, and the distal end of the sleeve is inserted through the incision and is inside the patient's body cavity and the access port projects a short distance above the patient's body.

5. An access port as claimed in claim 1, the sleeve has an area between the distal end and the proximal end on which, when the distal end of the sleeve is inserted through the incision, the patient's muscle tissue around the incision is adapted to act as sealing means for assisting in sealing the intermediate portion of the sleeve between the distal end and the proximal end.

6. An access port as claimed in claim 1, the inflatable chamber is arranged in surrounding relation to the sleeve and exerts a pressure on the sleeve causing at least a portion of it to collapse thereby sealing the entry opening.

7. An access port as claimed in claim 1, in which the sleeve and inflatable chamber are co-axial and include sheets of gas permeable flexible material bonded at their common proximal end and side edges, with the sleeve being within the inflatable chamber in the proximal region.

* * * * *